(12) United States Patent
Shibanuma et al.

(10) Patent No.: US 10,575,817 B2
(45) Date of Patent: Mar. 3, 2020

(54) ULTRASOUND DIAGNOSIS APPARATUS

(71) Applicant: Toshiba Medical Systems Corporation, Otawara-shi (JP)

(72) Inventors: Hiroyuki Shibanuma, Yaita (JP); Isao Uchiumi, Nasushiobara (JP); Nobuyuki Iwama, Nasushiobara (JP); Wataru Kameishi, Nasushiobara (JP); Yuhei Fukuo, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 398 days.

(21) Appl. No.: 15/427,553

(22) Filed: Feb. 8, 2017

(65) Prior Publication Data

US 2017/0252001 A1 Sep. 7, 2017

(30) Foreign Application Priority Data

Mar. 2, 2016 (JP) ................................. 2016-040519

(51) Int. Cl.
*A61B 8/14* (2006.01)
*A61B 8/00* (2006.01)

(52) U.S. Cl.
CPC ............ *A61B 8/145* (2013.01); *A61B 8/4488* (2013.01); *A61B 8/54* (2013.01)

(58) Field of Classification Search
CPC .......... A61B 8/145; A61B 8/54; A61B 8/4488
(Continued)

(56) References Cited

U.S. PATENT DOCUMENTS

| | | | | | |
|---|---|---|---|---|---|
| 4,199,246 | A | * | 4/1980 | Muggli | G01S 15/104 352/140 |
| 5,319,974 | A | * | 6/1994 | Lenz | G01F 1/002 181/124 |

(Continued)

FOREIGN PATENT DOCUMENTS

| | | |
|---|---|---|
| JP | 6-154210 | 6/1994 |
| JP | 2004-329626 A | 11/2004 |

(Continued)

OTHER PUBLICATIONS

Japanese Office Action dated Oct. 15, 2019 in Patent Application No. 2016-040519.

*Primary Examiner* — Sanjay Cattungal
(74) *Attorney, Agent, or Firm* — Oblon, McClelland, Maier & Neustadt, L.L.P.

(57) ABSTRACT

According to one embodiment, an ultrasound diagnosis apparatus transmits ultrasound waves to a subject from a plurality of transducers each corresponding to one of a plurality of channels, and receives reflected waves generated in the subject by the transducers. The ultrasound diagnosis apparatus includes a control circuit and a receiving circuit. The control circuit controls channels used to transmit ultrasound waves and channels not used to transmit ultrasound waves among the channels. The receiving circuit receives the reflected waves, and includes a preamplifier and an impedance control circuit. The preamplifier amplifies the reflected waves. The impedance control circuit is located on the upstream side of the preamplifier, and sets line impedance in a transmitting period, in which the ultrasound waves are transmitted from the transducers to the inside of the subject, to be lower than that in a receiving period, in which the reflected waves are received by the transducers.

12 Claims, 7 Drawing Sheets

(58) Field of Classification Search
USPC .................................................. 600/437–469
See application file for complete search history.

(56) References Cited

U.S. PATENT DOCUMENTS

| | | | | |
|---|---|---|---|---|
| 6,540,677 | B1* | 4/2003 | Angelsen | B06B 1/0215 |
| | | | | 310/314 |
| 7,791,254 | B1* | 9/2010 | Gibson | G01H 11/08 |
| | | | | 310/336 |
| 8,058,776 | B1* | 11/2011 | Gibson | G01H 11/08 |
| | | | | 310/334 |
| 2002/0156379 | A1* | 10/2002 | Angelsen | B06B 1/0614 |
| | | | | 600/459 |
| 2004/0000841 | A1* | 1/2004 | Phelps | B06B 1/0622 |
| | | | | 310/314 |
| 2005/0113694 | A1* | 5/2005 | Haugen | A61B 8/14 |
| | | | | 600/443 |
| 2005/0113698 | A1* | 5/2005 | Kristoffersen | G01S 7/52079 |
| | | | | 600/459 |
| 2005/0113699 | A1* | 5/2005 | Haugen | G01S 7/52079 |
| | | | | 600/459 |
| 2006/0068834 | A1* | 3/2006 | Jones | A61B 8/00 |
| | | | | 455/550.1 |
| 2009/0227872 | A1* | 9/2009 | Pan et al. | A61B 8/481 |
| | | | | 600/458 |
| 2011/0201936 | A1* | 8/2011 | Miyajima | G01S 7/52023 |
| | | | | 600/459 |
| 2014/0211592 | A1 | 7/2014 | Miyazawa | |

FOREIGN PATENT DOCUMENTS

| | | |
|---|---|---|
| JP | 2011-161167 A | 8/2011 |
| JP | 2012-254216 A | 12/2012 |
| JP | 2014-94111 | 5/2014 |

* cited by examiner

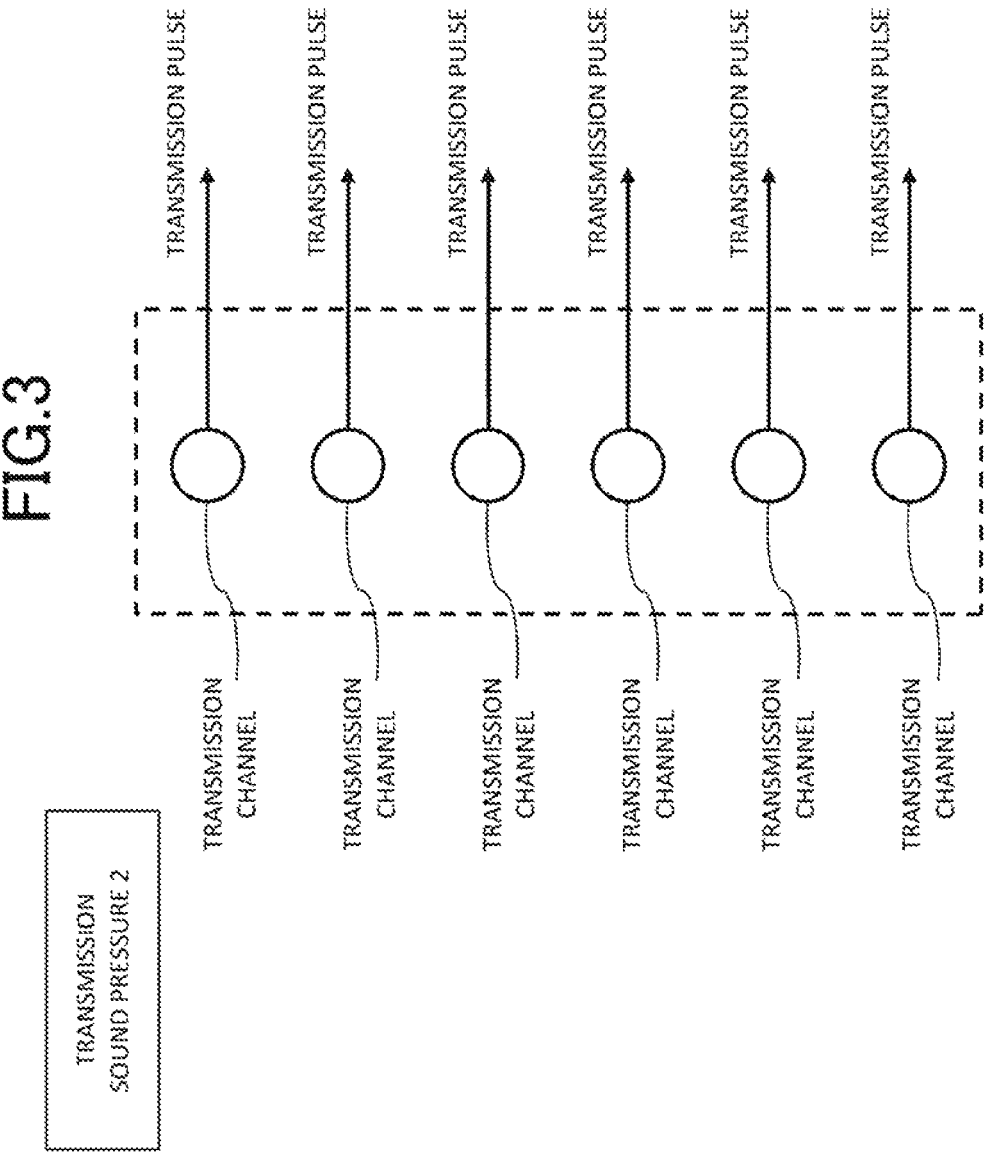

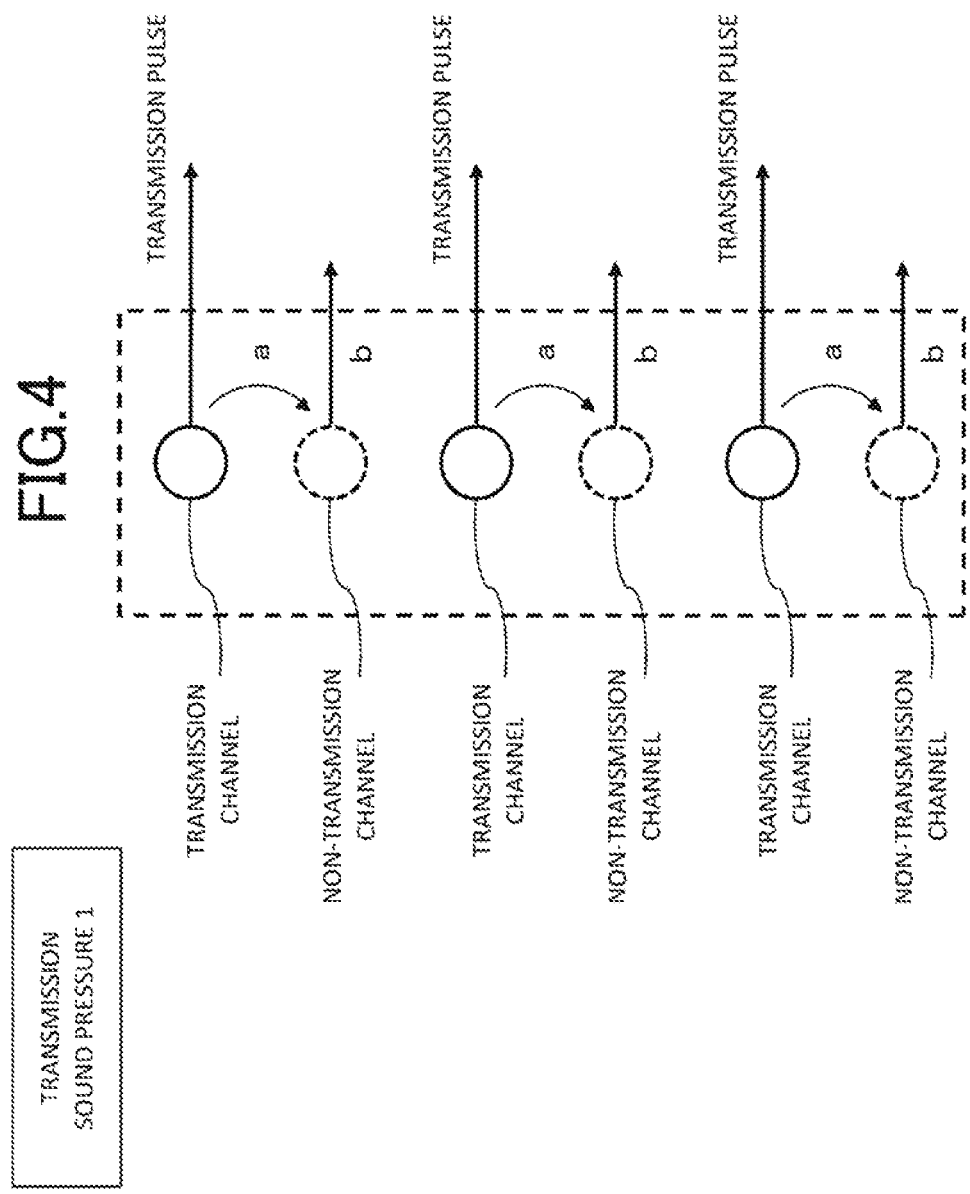

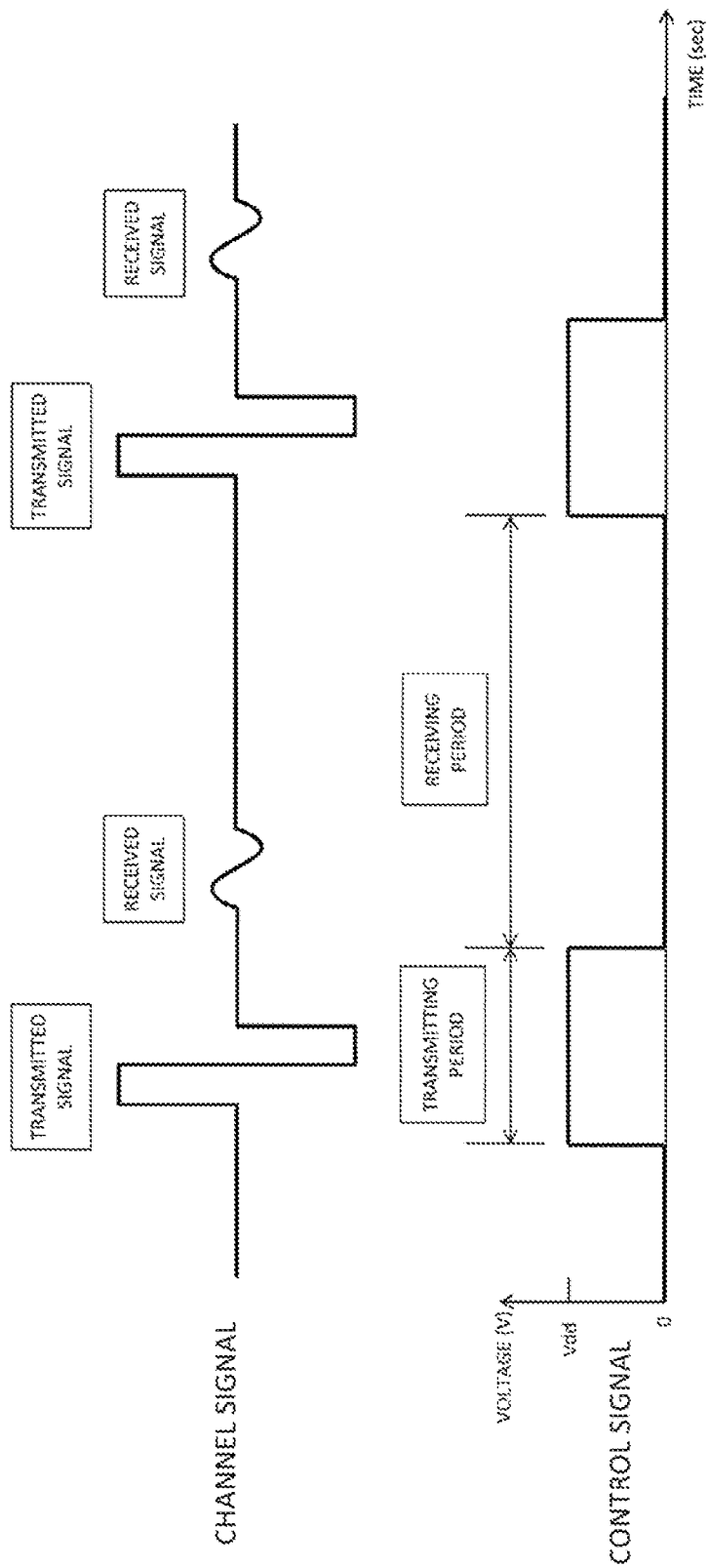

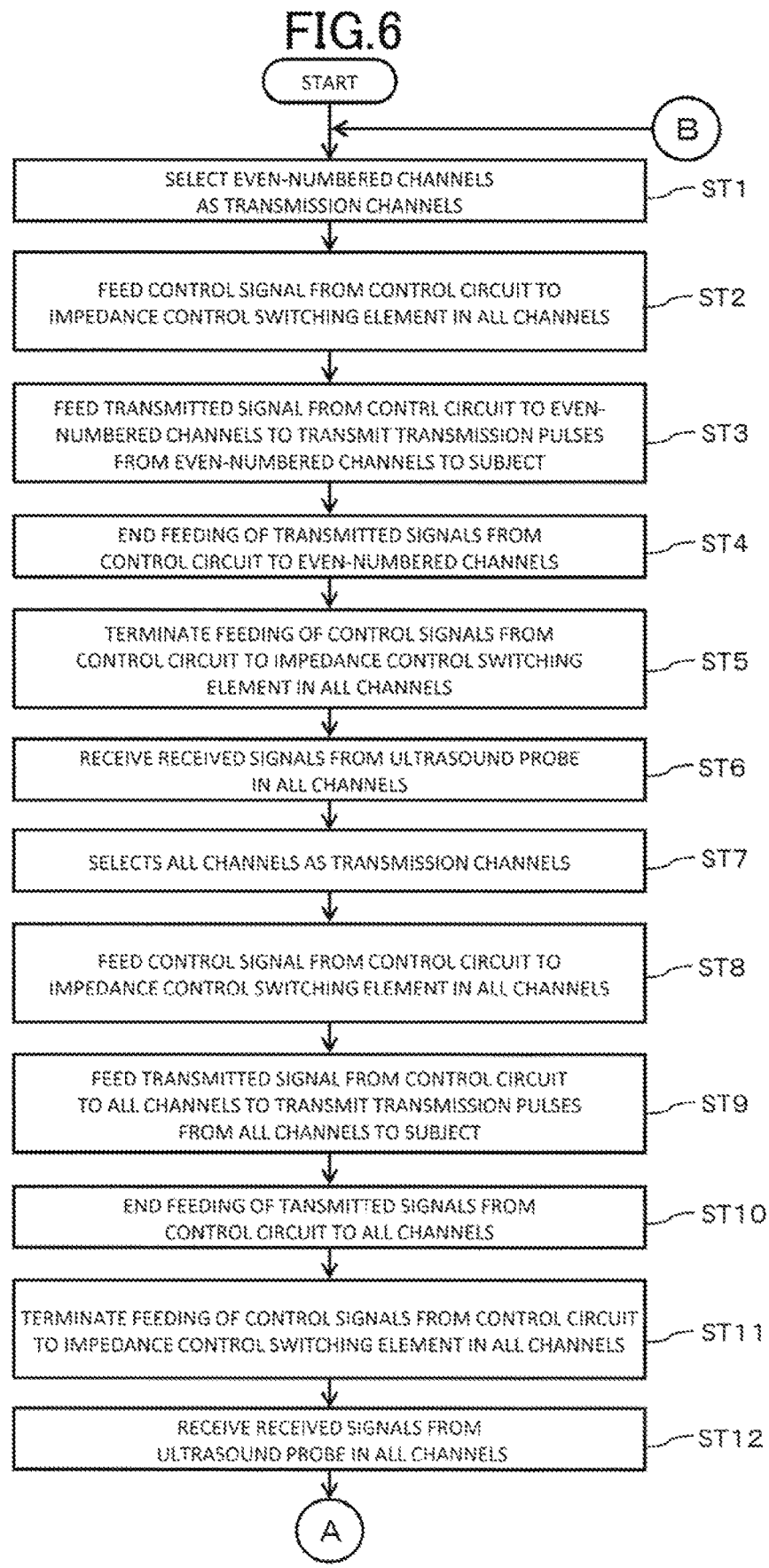

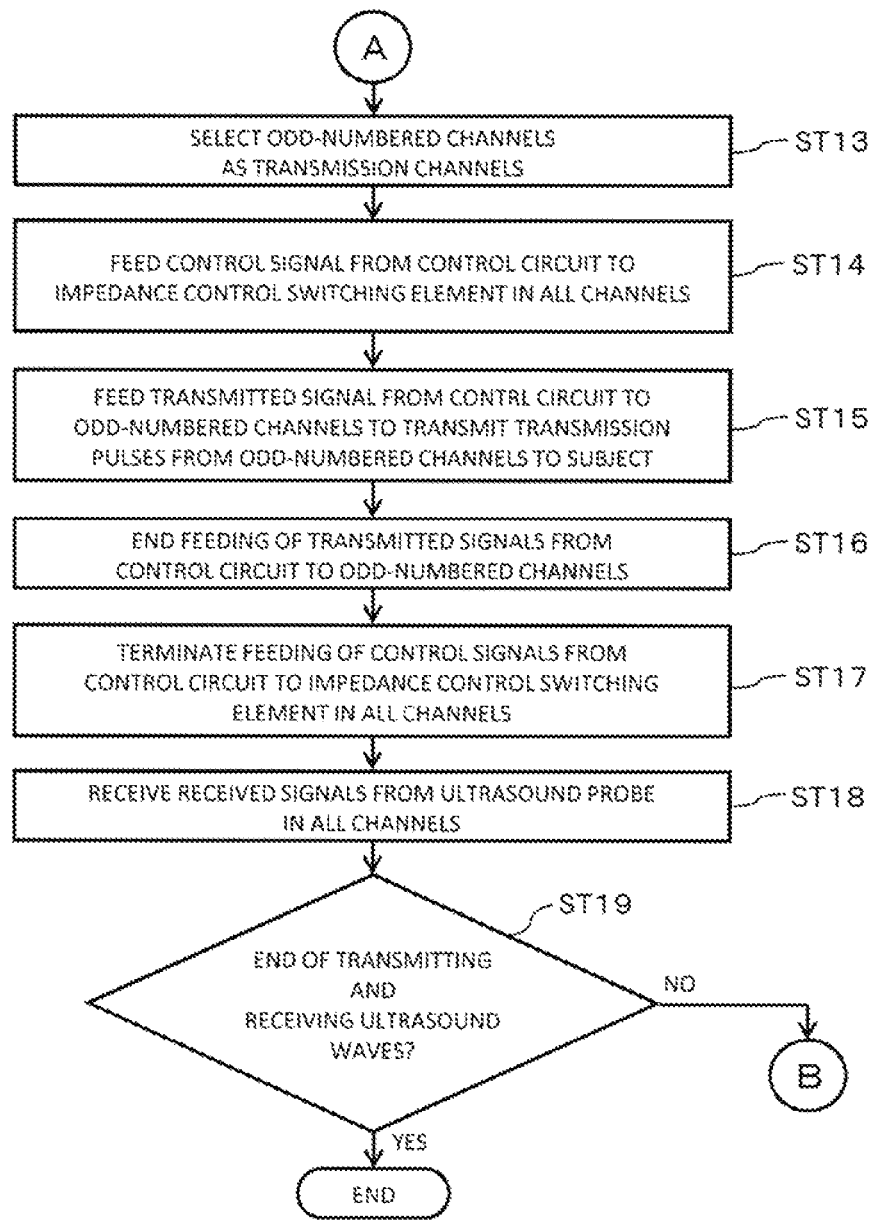

ULTRASOUND DIAGNOSIS APPARATUS

CROSS-REFERENCE TO RELATED APPLICATION

This application is based upon and claims the benefit of priority from Japanese Patent Application No. 2016-040519, filed on Mar. 2, 2016; the entire contents of which is incorporated herein by reference.

FIELD

Embodiments described herein relate generally to an ultrasound diagnosis apparatus.

BACKGROUND

In the medical field, the ultrasound diagnosis apparatus is used for various diagnoses and treatments because it can investigate the internal structure, blood flow state, and the like of the subject non-invasively. The ultrasound diagnosis apparatus transmits ultrasound waves into the body from an ultrasound probe having a transducer (piezoelectric transducer) at its tip and brought into contact with the body surface of the subject. Then, the transducer of the ultrasound probe receives reflected waves caused by the acoustic impedance mismatch inside the subject. The ultrasound diagnosis apparatus generates an ultrasound image based on the received signal obtained in this way.

When the ultrasound diagnosis apparatus generates the ultrasound image, the reflected waves (received echo) received by the transducer are amplified by a preamplifier in a receiving circuit. However, unless appropriate gain control is performed on the preamplifier, the preamplifier saturates, and an appropriate ultrasound image is not to be generated and displayed. As described above, the ultrasound diagnosis apparatus generates the ultrasound image using the reflected waves received from the subject, and therefore, is required to transmit and receive ultrasound waves as accurate as possible.

Meanwhile, in recent years, a technique called harmonic imaging has been developed. The harmonic imaging uses a nonlinear component detected in a trace amount when a sound wave propagates with respect to the generation of an ultrasound image. An ultrasound wave has the property that it propagates in a high sound pressure part at a higher speed than in a low sound pressure part. Therefore, even if the transmitted ultrasound waves are sinusoidal waves composed of reference wave components, the distortion gradually occurs in the course of the propagation. As a result, the ultrasound waves include harmonic waves having nonlinear components.

Examples of the harmonic imaging using harmonic components include contrast harmonic imaging (CHI). In CHI, a subject is administered a contrast medium containing microbubbles for ultrasound waves to image harmonic components generated when the microbubbles resonate and collapse.

Therefore, in CHI, it is necessary to use microbubbles without destroying them. However, even in the case of ultrasound irradiation used in normal diagnosis, the microbubbles can be destroyed by the mechanical action of ultrasound waves. If the microbubbles are destroyed, the intensity of reflected signals is deteriorated. Therefore, in order not to destroy the microbubbles as much as possible, there is a demand for imaging by ultrasound transmission at a low sound pressure level. On the other hand, the imaging by ultrasound transmission at a low sound pressure level raises concerns about the reduction in S/N ratio.

In CHI, reference wave components and higher harmonic components are separated by filtering and waveform computation to extract harmonic components. Although there are various methods for extracting the harmonic components, in order to solve the problem in imaging by ultrasound transmission of low sound pressure, for example, a method called amplitude modulation is used. In the amplitude modulation method, ultrasound waves are transmitted three times such that the ratio of the relative sound pressures of them becomes 1:2:1. Then, the sum of two received signals having a transmission sound pressure 1 is subtracted from a received signal having a sound pressure 2 to remove the reference wave components, thereby extracting the harmonic components.

In this manner, in CHI, ultrasound waves are transmitted and received a plurality of times with different sound pressures to extract the harmonic components. In order to set the transmission sound pressures 1 and 2 to different values, voltages applied to transducers may be set to different values; however, it is difficult to set the applied voltages to different values with high accuracy. Therefore, all the transducers are operated for the transmission sound pressure 2, while half of the transducers are operated for the transmission sound pressure 1 to adjust the sound pressure. In the case of setting the transmission sound pressure 1, to match the transmission apertures with those of the transmission sound pressure 2, odd-numbered or even-numbered transducers (i.e., every other channels) of the transducer array are operated.

BRIEF DESCRIPTION OF THE DRAWINGS

FIG. 3 is a schematic diagram for explaining transmission channels and non-transmission channels of the embodiment;

FIG. 4 is a schematic diagram for explaining transmission channels and non-transmission channels of the embodiment;

FIG. 5 is a waveform diagram illustrating a relationship between a signal waveform upon transmitting and receiving ultrasonic waves and a waveform of a control signal to an impedance control switching element in an impedance control circuit upon transmitting and receiving in the embodiment;

FIG. 6 is a flowchart illustrating a flow of control when ultrasonic waves are transmitted and received in the embodiment; and FIG. 7 is a flowchart illustrating a flow of control when ultrasonic waves are transmitted and received in the embodiment.

DETAILED DESCRIPTION

Figure 1:
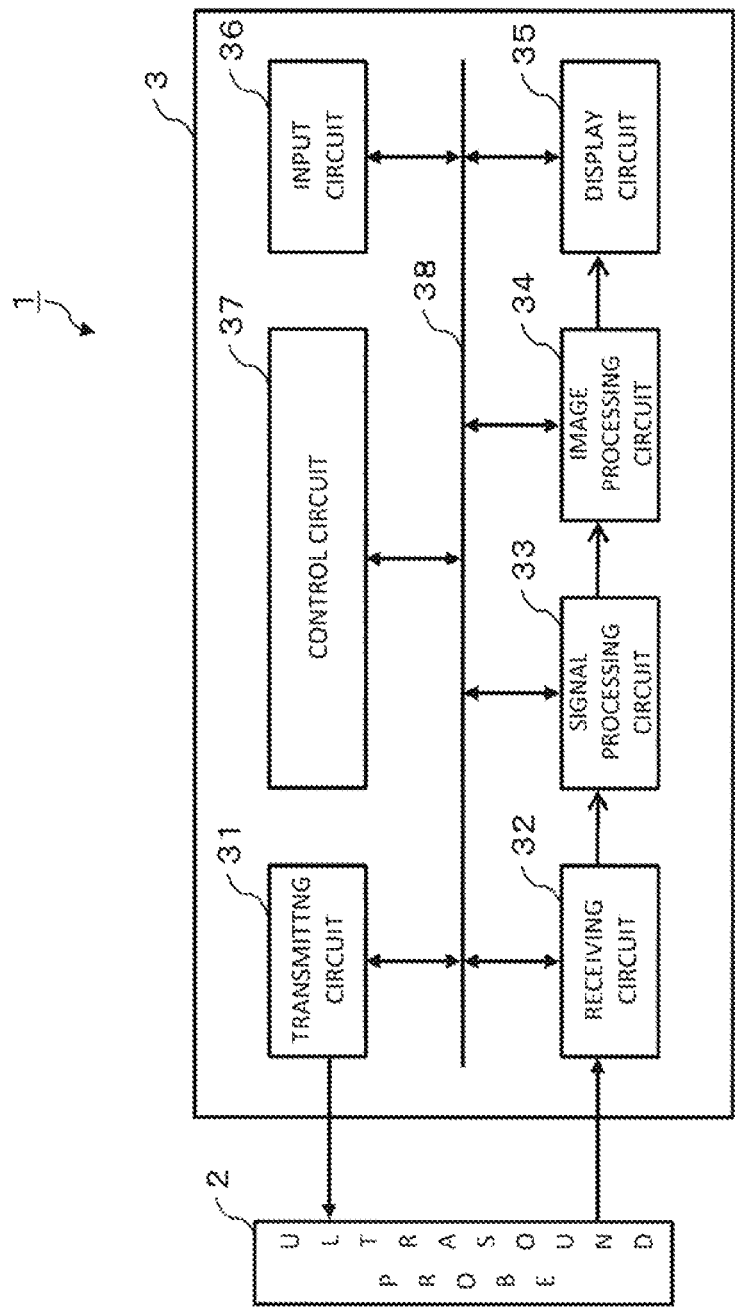
FIG. 1 is a block diagram illustrating the overall configuration of an ultrasound diagnosis apparatus according to an embodiment.

In general, according to one embodiment, an ultrasound diagnosis apparatus is configured to transmit ultrasound waves to the inside of a subject from a plurality of transducers each corresponding to one of a plurality of channels, and receive reflected waves generated in the subject by the transducers. The ultrasound diagnosis apparatus includes a control circuit and a receiving circuit. The control circuit is configured to control channels used to transmit ultrasound waves and channels not used to transmit ultrasound waves among the channels. The receiving circuit is configured to receive the reflected waves, and includes a preamplifier and an impedance control circuit. The preamplifier is configured to amplify the reflected waves. The impedance control circuit is located on the upstream side of the preamplifier, and is configured to set line impedance in a transmitting period, in which the ultrasound waves are transmitted from the transducers to the inside of the subject, to be lower than that in a receiving period, in which the reflected waves are received by the transducers.

Referring now to the drawings, a description is given of an ultrasound diagnosis apparatus according to embodiments.

[Configuration of Ultrasound Diagnosis Apparatus]

FIG. 1 is a block diagram illustrating the overall configuration of an ultrasound diagnosis apparatus 1 according to an embodiment. As illustrated in FIG. 1, the ultrasound diagnosis apparatus 1 includes an ultrasound probe 2 for transmitting and receiving ultrasound waves to and from a subject, and a main body 3 to which the ultrasound probe 2 is detachably connected.

The ultrasound probe 2 transmits and receives ultrasound waves in a state where its distal end surface is in contact with the surface of the subject. The ultrasound probe 2 has a plurality of built-in piezoelectric transducers, which are one-dimensionally arranged in the distal end surface. The ultrasound probe 2 transmits ultrasound waves into the subject from each of the piezoelectric transducers to scan a scan area, and receives reflected waves from the subject as echo signals. Examples of the scan include B mode scan and Doppler mode scan.

In addition, the ultrasound probe 2 has a sector scan correspondence, a linear scan correspondence, a convex scan correspondence, and the like, which are arbitrarily selected according to a diagnosis site. Besides, the transducers array is not limited to the one-dimensional array. When the transducers are two-dimensionally arranged, the volume data can be acquired in real time. In the case of obtaining a three-dimensional stereoscopic image, a 3D scanning probe is used as the ultrasound probe 2. Examples of the 3D scanning probe include 2D array probes, mechanical 4D probes, and the like.

The main body 3 includes therein a transmitting circuit 31, a receiving circuit 32, a signal processing circuit 33, an image processing circuit 34, a display circuit 35, an input circuit 36, and a control circuit 37 that controls each of them. The transmitting circuit 31 transmits a drive signal to the ultrasound probe 2. The receiving circuit 32 receives a reflected signal from the ultrasound probe 2. The signal processing circuit 33 processes the reflected signal. The image processing circuit 34 generates an ultrasound image. The display circuit 35 displays various images. The input circuit 36 receives input operation from the operator such as an examiner. These circuits are connected to a bus 38 and capable of exchanging various signals.

The main body 3 may be connected to another image diagnosis apparatus (modality), an image server, an image processing apparatus, or the like via a communication network. Information can be communicated via the communication network using any standard such as digital imaging and communications in medicine (DICOM).

Under the control of the control circuit 37, the transmitting circuit 31 generates a drive signal for generating ultrasound waves in the ultrasound probe 2, that is, an electric pulse signal (hereinafter referred to as "drive pulse") to be applied to each of the piezoelectric transducers. The transmitting circuit 31 transmits the drive pulse generated to the ultrasound probe 2. The transmitting circuit 31 includes various circuits such as a reference pulse generating circuit, a delay control circuit, a drive pulse generating circuit, and the like (not illustrated), and the circuits implement the above-described functions.

The receiving circuit 32 receives a reflected signal, that is, an echo signal, from the ultrasound probe 2. The receiving circuit 32 performs phase addition on the received signal, and outputs the signal acquired by the phasing addition to the signal processing circuit 33.

Figure 2:
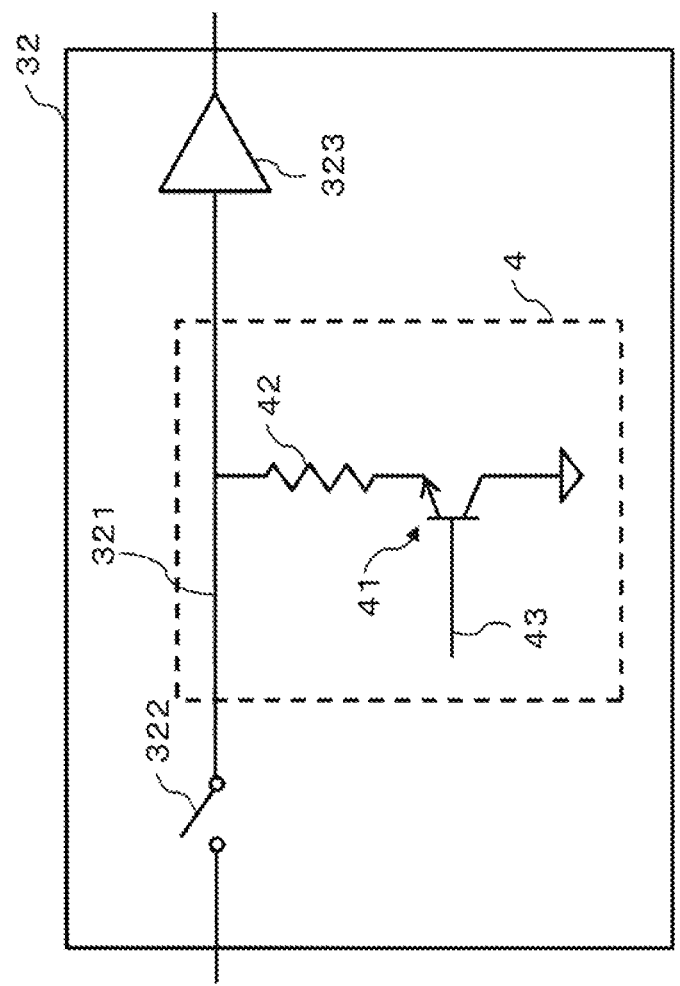
FIG. 2 is a block diagram illustrating the internal structure of a receiving circuit of the embodiment.

FIG. 2 is a block diagram illustrating the internal structure of the receiving circuit 32 of the embodiment. The receiving circuit 32 has a receiving echo signal line 321 connected to the transducers for sending the received echo signal to the signal processing circuit 33. A line switching element 322 and a preamplifier 323 are connected to the receiving echo signal line 321; the line switching element 322 is connected to the upstream side (a position close to the transducers), while the preamplifier 323 is connected to the downstream side (a position close to the signal processing circuit 33).

The line switching element 322 switches on and off the connection between the receiving circuit 32 and the transducers. Therefore, when the line switching element 322 is ON, reflected waves are received. On the other hand, when the line switching element 322 is OFF, reflected waves are not received. In addition, the preamplifier 323 is configured to amplify the reflected waves transmitted from the transducers and received through the receiving echo signal line 321.

Although FIG. 2 illustrates only the line switching element 322 and the preamplifier 323 connected to the receiving echo signal line 321, for example, a capacitor may be connected to the upstream side of the preamplifier 323.

In the receiving circuit 32 of the embodiment, an impedance control circuit 4 is connected to the receiving echo signal line 321 between the line switching element 322 and the preamplifier 323. The impedance control circuit 4 reduces the adverse effect caused by the crosstalk to the non-transmitting channel when ultrasound waves are transmitted to the inside of the subject from the transmitting circuit 31 through the transducers by the amplitude modulation.

The impedance control circuit 4 includes an impedance control switching element 41. In the impedance control switching element 41, an emitter is connected to the receiving echo signal line 321, and a collector is grounded to the ground.

In the embodiment, resistors 42 are arranged between the impedance control switching element 41 and the receiving echo signal line 321. One of the resistors 42 is connected to the emitter of the impedance control switching element 41, and the other is connected to the receiving echo signal line 321. An input line 43 for inputting a control signal from the control circuit 37 is connected to the base of the impedance control switching element 41.

Referring back to FIG. 1, the signal processing circuit 33 generates various types of data using a received signal supplied from the receiving circuit 32, and outputs the data to the image processing circuit 34 and the control circuit 37. The signal processing circuit 33 includes, for example, a B mode processing circuit (or a Bc mode processing circuit), a Doppler mode processing circuit, a color Doppler mode processing circuit, and the like (not illustrated). The B mode processing circuit visualizes the amplitude information of the received signal, and generates data of a B mode signal. The Doppler mode processing circuit extracts Doppler shift frequency components from the received signal, and applies the fast Fourier transform (FFT) and the like to generate Doppler signal data of blood flow information. The color Doppler mode processing circuit visualizes the blood flow information based on the received signal, and generates data of the color Doppler mode signal.

Based on the data supplied from the signal processing circuit 33, the image processing circuit 34 generates a two-dimensional or three-dimensional ultrasound image of the scan region. For example, the image processing circuit 34 generates volume data related to the scan area from the data supplied. Then, from the volume data thus generated, the image processing circuit 34 generates data of a two-dimensional ultrasound image by multi-sectional reconstruction method (MPR) or data of a three-dimensional ultrasound image by volume rendering. The image processing circuit 34 outputs the two-dimensional or three-dimensional ultrasound image thus generated to the display circuit 35. Examples of the ultrasound image include a B mode image, a Doppler mode image, a color Doppler mode image, an M mode image, and the like.

The display circuit 35 displays various images such as an ultrasound image generated by the image processing circuit 34, an operation screen (e.g., graphical user interface (GUI) for receiving various instructions from the operator), and the like under the control of the control circuit 37. As the display circuit 35, for example, a liquid crystal display, an organic electroluminescence (EL) display, or the like can be used.

The input circuit 36 receives various inputs by the operator such as instructions for imaging, image display, switching images, designating the mode, various settings, and the like. As the input circuit 36, for example, a GUI or an input device such as buttons, a keyboard, a trackball, or the like can be used.

The control circuit 37 has a memory (not illustrated), and controls the respective parts of the ultrasound diagnosis apparatus 1 in a comprehensive manner. For example, the control circuit 37 controls the impedance in the receiving circuit 32 when ultrasound waves are transmitted and received via the transmitting circuit 31 and the receiving circuit 32. In addition, the control circuit 37 performs control to store data supplied from the signal processing circuit 33, data obtained by predetermined processing, and the like in the storage circuit, and to display an image on the display circuit 35.

For example, the transmitting circuit 31 can be realised by software that causes a processor to execute a program stored in a predetermined memory or the like. The term "processor" as used herein refers to, for example, a dedicated or general purpose a central processing unit (CPU), an arithmetic circuit (circuitry), an application specific integrated circuit (ASIC), a programmable logic device (e.g., simple programmable logic device (SPLD), a complex programmable logic device (CPLD), and a field-programmable gate array (FPGA)), and the like.

The processor reads out a program stored in the memory or directly embedded in the circuit of the processor and executes it, thereby realizing the functions. The memory for storing the program may be provided separately for each processor or may be, for example, one that stores programs corresponding to the functions of the signal processing circuit 33 illustrated in FIG. 1. For example, a storage device such as a general random access memory (RAM) or a hard disc drive (HDD) is applied to the configuration of the memory.

The control circuit 37 controls the transmitting circuit 31 based on a control signal for forming a drive pulse, and a control signal for distinguishing between a transmitting period and a receiving period. The transmitting circuit 31 generates a drive pulse for forming a transmission pulse from each of the transducers based on a combination of the control signals. Besides, based on the combination of the control signals, the transmitting circuit 31 selects, from the transducers, those that transmit the transmission pulse and those that do not.

The transmitting circuit 31 selects transducers that transmit the transmission pulse and transducers that do not to control the transmission sound pressure. For example, assuming that the sound pressure is 2 when a transmission pulse is transmitted from all the transducers at the time of transmission, in the case of transmitting the transmission pulse at a transmission sound pressure such that the sound pressure relatively becomes 1, odd-numbered or even-numbered transducers are assigned as those that do not perform transmission. Upon receiving, the reflected waves (received echo) from the subject, are received by both the transmitting transducers and the non-transmitting transducers.

The transmitting circuit 31 generates drive pulses having waveforms different from each other in voltage and polarity for driving the transducers based on the delayed reference pulse. The drive pulse is generated for each of the transducers, and is applied to corresponding one of the transducers. Thereby, a transmission pulse is transmitted from each of the transducers to the inside of the subject. That is, in the transmitting circuit 31, a circuit that generates the drive pulse is paired with a transducer to which the drive pulse is applied. Hereinafter, a transducer that transmits the transmission pulse and the circuit that generates the drive pulse corresponding to the transducer are collectively referred to as "channel". In addition, the channel that performs transmission is referred to as "transmission channel", and the channel that does not as "non-transmission channel".

The drive pulse is an electric pulse applied to the transducer and is a bipolar pulse signal corresponding to a waveform transmitted from the transducer. The voltage of the drive pulse determines the sound pressure of ultrasound waves to be transmitted. Further, the burst frequency and burst count of the drive pulse determines the frequency of and burst count of the ultrasound waves.

FIGS. 3 and 4 are schematic diagrams for explaining transmission channels and non-transmission channels of the embodiment. In FIGS. 3 and 4, each channel is illustrated as a circle. Circles drawn by solid line represent transmission channels, and those drawn by broken line represent non-transmission channels. A transmission pulse is transmitted from the transmission channels to the inside of the subject. In FIGS. 3 and 4, this transmission is indicated by arrows extending rightward from the solid circles that represent the transmission channels.

In the case of using amplitude modulation in CHI, the transmission sound pressure is changed by controlling the number of transmission channels. For example, FIG. 3 illustrates a case of the transmission sound pressure "2", while FIG. 4 illustrates a case of the transmission sound pressure "1", which is ½ of the case illustrated in FIG. 3. Although FIGS. 3 and 4 illustrate only six channels for convenience of explanation, actually, there are more channels, for example, 128 channels or the like.

As illustrated in FIG. 3, in the case of the transmission sound pressure "2" all the channels are used as the transmission channels, and a transmission pulse is transmitted from all the channels.

On the other hand, as illustrated in FIG. 4, in the case of the transmission sound pressure "1", for example, the odd-numbered channels are assigned to the transmission channels, and the even-numbered channels are assigned to the non-transmission channels. The assignment to the transmission channels and the non-transmission channels is alternately switched between the odd-numbered channels and the even-numbered channels for every transmission. A transmission pulse is transmitted from the transducers assigned to the transmission channels.

The non-transmission channels in FIG. 4 are influenced by crosstalk (leakage of transmitted signals) from the adjacent transmission channels as indicated by arrows a. As described above, when used as a non-transmission channel, no drive pulse is generated, and therefore a drive pulse is not applied to the corresponding transducer. Therefore, a transmission pulse is not transmitted from the transducer of the non-transmission channel. Nevertheless, a voltage is sometimes applied to the transducers of the non-transmission channels due to the crosstalk from the transmission channels. As a result, unintended transmission pulses are generated from the transducers assigned to the non-transmission channels as indicated by arrows b. Due to the influence of the crosstalk on the non-transmission channels from the transmission channels, actual output of the transmission sound pressure may become larger than "1" in some cases.

With reference to FIG. 3, in order to simplify the explanation, an example is described in which all the channels existing in the ultrasound probe 2 perform transmission alternately between odd-numbered channels and even-numbered channels. However, in actual ultrasound probes, the number of transducers to be used may be determined according to the opening width, and transducers that are not used according to the opening width are present as non-transmission channels. Therefore, crosstalk may occur in transducers that are not selected to form the opening. As described above, transducers to be used are determined according to the opening width. The positions of the transducers to be used are changed for each transmission such that they are evenly used. For example, control is performed such that the transducers are used while being shifted by a predetermined number of transducers with respect to each transmission pulse, and in the beginning, the transducers not selected for the opening range are sequentially used.

In the embodiment, the line impedance is controlled in the receiving echo signal line 321 of the receiving circuit 32 to prevent the image deterioration due to the crosstalk occurring between the transmission channels and the non-transmission channels.

[Operation]

Next, with reference to FIGS. 2 and 5, a description is given of the operation of controlling the line impedance in the receiving echo signal line 321 of the receiving circuit 32.

As described above, when transmission pulses are transmitted from the transmission channels, the non-transmission channels are affected by the crosstalk from the adjacent transmission channels. As a result, unintended transmission pulses are transmitted to the subject from the non-transmission channels that are originally not supposed to transmit transmission pulses. Therefore, to reduce the transmission of the transmission pulses from the non-transmission channels, control may be performed such that the non-transmission channels are not affected by the crosstalk from the transmission channels.

Described below is control in the non-transmission channels adjacent to the transmission channels. When transmission pulses are transmitted from the transmission channels to the subject, no transmission pulse is transmitted from the non-transmission channels to the subject. In other words, the non-transmission channels are in a state of receiving reflected waves from the subject.

Therefore, in the receiving echo signal line 321 of the receiving circuit 32, the line switching element 322 is ON, and the transducers and the receiving circuit 32 are connected. When the receiving echo signal line 321 is in this state, the impedance of the receiving echo signal line 321 viewed from the transducers is the line impedance of the preamplifier.

When the receiving circuit 32 receives transmission crosstalk from the transmission channels in the non-transmission channels in such a state, a transmitted signal divided by impedance between signal lines and the original line impedance in the receiving echo signal line 321 appears in the receiving echo signal line 321. In order to avoid the influence of the crosstalk, the impedance control circuit 4 provided to the receiving echo signal line 321 is used to keep the impedance of the receiving echo signal line 321 low.

FIG. 5 is a waveform diagram illustrating a relationship between a signal waveform upon transmitting and receiving ultrasonic waves and a waveform of a control signal to the impedance control switching element 41 in the impedance control circuit 4 upon transmitting and receiving.

The upper part of FIG. 5 illustrates the waveform of a transmitted signal transmitted from the control circuit 37 to the transmission channels for transmitting ultrasound waves from the transmission channels to the subject, and the waveform of a received signal when the transmission channels receive reflected waves. The lower part of FIG. 5 illustrates ON and OFF of the control signal input from the control circuit 37 to the impedance control switching element 41 via the input line 43.

In both the upper and lower waveform diagrams, the horizontal axis represents time (sec). In the lower part, the vertical axis represents the voltage (v) of the control signal input to the impedance control switching element 41. Further, Vdd (v) represents the voltage of the control signal input from the control circuit 37 to the impedance control switching element 41.

The control circuit 37 transmits a control signal to the impedance control switching element 41 before transmission pulses are actually transmitted from the transducers in the transmission channels to the subject. Upon receipt of the control signal from the control circuit 37, the impedance control switching element 41 is turned on. When the impedance control switching element 41 is turned on, the receiving echo signal line 321 and the ground are connected.

In the impedance control circuit 4, the impedance control switching element 41 is connected to the resistor 42. Therefore, when the impedance control switching element 41 is turned on, the line impedance in the receiving echo signal line 321 becomes the impedance of the resistor 42.

As described above, when the impedance control switching element 41 is OFF, the line impedance in the receiving echo signal line 321 becomes the line impedance of the preamplifier 323. Although the line impedance of the preamplifier 323 is selected according to the band desired to be generated as an ultrasound image, high impedance is maintained. In the case generating an ultrasound image by the use of reflected waves received by the receiving circuit 32, if the line impedance in the receiving circuit 32 is low, the receiving sensitivity is reduced, and a desired ultrasound image cannot be generated. Therefore, it is necessary to keep the line impedance in the receiving echo signal line 321 high at least while the receiving echo signal is being received.

While the transmission pulses are being transmitted from the transducers of the ultrasound probe 2 to the subject, the ultrasound probe 2 does not receive the reflected waves. Therefore, in this state, by setting the line impedance in the receiving echo signal line 321 to a sufficiently low value, it is possible to reduce the influence of the crosstalk from the transmission channels as much as possible.

Therefore, by connecting the receiving echo signal line 321 to the ground, the line impedance in the receiving echo signal line 321 can be made zero. If the line impedance of the receiving circuit 32 can be made zero, there is no influence of the crosstalk from the transmission channels, and the non-transmission channels are prevented from transmitting unintended transmission pulses when transmission pulses are transmitted from the transmission channels.

However, if the receiving echo signal line 321 has a direct current (DC) potential, when the impedance control switching element 41 is turned on and the receiving echo signal line 321 of the receiving circuit 32 is connected to the ground, the impedance control switching element 41 itself may not be able to withstand the current flowing therethrough. Therefore, in the impedance control circuit 4 of the embodiment, the resistor 42 is connected between the impedance control switching element 41 and the receiving echo signal line 321.

When the impedance control switching element 41 is turned on, the line impedance in the receiving echo signal line 321 becomes the impedance indicated by the resistor 42. Hence, by connecting the low-impedance resistor 42, the line impedance in the receiving echo signal line 321 can be set to a sufficiently low value as compared to the original line impedance in the receiving echo signal line 321. Consequently, even if crosstalk occurs from adjacent transmission channels, the impedance in the receiving echo signal line 321 can be kept low. In addition, the current flowing through the impedance control switching element 41 is relieved due to the connection to the resistor 42, which leads to the protection of the impedance control switching element 41.

The impedance control switching element 41 continues to receive control signals from the control circuit 37 for a while even after the end of the transmission from the transmission channels. In this manner, not only a period when transmitted signals are actually sent to the transmission channels but also periods before and after the transmission are included in the transmitting period of transmission pulses from the transmission channels, and the impedance control switching element 41 keeps receiving control signals from the control circuit 37. Thereby, it is possible to sufficiently eliminate the influence of crosstalk from live transmission channels to the non-transmission channels.

When the transmitting period ends, the line impedance in the receiving echo signal line 321 is no longer required to be low. Thus, the control circuit 37 terminates feeding control signals to the impedance control switching element 41. The period from here to the start of the next transmitting period is the receiving period. In the receiving period, reflected waves from the transducers, which are the basis of image generation, are received, and, as described above, the line impedance in the receiving echo signal line 321 of the receiving circuit 32 needs to be maintained at a high level. Therefore, the impedance control switching element 41 is turned off to cut off the connection between the receiving echo signal line 321 and the ground. Thus, the line impedance in the receiving echo signal line 321 can be set to the line impedance of the preamplifier 323, that is, high impedance.

Since the impedance of the receiving echo signal line 321 is kept high, even when both the transmission channels and the non-transmission channels receive reflected waves from the subject, the receiving circuit 32 can receive the waves with high sensitivity.

A description has been given of the control for reducing the influence of the crosstalk that the non-transmission channels receive from the transmission channels in the receiving circuit 32. Meanwhile, it is also necessary to consider the control over the receiving circuit 32 corresponding to the transmission channels.

When a drive pulse is applied to a transducer in a transmission channel and a transmission pulse is transmitted to the subject, the line switching element 322 connected to the receiving echo signal line 321 of the receiving circuit 32 corresponding to the transmission channel is turned off. This is because if the line switching element 322 is ON in the transmission channel, the receiving circuit 32 is affected when a drive pulse is applied to the transducer.

When the line switching element 322 in the receiving echo signal line 321 of the receiving circuit 32 corresponding to the transmission channel is controlled to be OFF, the transmitting circuit 31 and the receiving circuit 32 in the transmission channel are not connected and separated from each other. Therefore, even if the receiving echo signal line 321 is connected to the ground, it is unlikely to influence the transmission of transmission pulses from the transmission channels to the subject.

Therefore, during the transmitting period of transmission pulses from the transmission channels to the subject, the impedance control switching element 41 of the impedance control circuit 4 in the receiving circuit 32 corresponding to each of the transmission channels is turned on. Then, as described above, the line impedance of the receiving echo signal line 321 is kept low.

In view of the above, during the transmitting period in which the transmission pulses are transmitted from the transmission channels to the subject, impedance control circuit 4 is controlled to maintain the line impedance of the receiving circuit 32 in all of the transmission channels and the non-transmission channels at a low level regardless of whether they are odd-numbered or even-numbered channels.

Referring again to FIG. 5, when a transmitted signal (drive pulse) is applied to the transducers as a channel signal, the control signal is applied to the impedance control switching element 41 assuming that it is in the transmitting period of transmission pulses. As a result, the impedance control switching element 41 is turned on, and the receiving echo signal line 321 is connected to the ground. Thereby, the line impedance in the receiving echo signal line 321 can be made lower than that when the receiving echo signal line 321 is not connected to the ground.

In the state of receiving reflected waves (echo signals) after the end of the transmitting period, the feeding of the control signals to the impedance control switching element 41 is terminated, and the impedance control switching element 41 is turned off. As a result, the line impedance of the receiving echo signal line 321 can be made high. Thus, the reflected waves can be received with high sensitivity.

Next, with reference to the flowcharts illustrated in FIGS. 6 and 7, a description is given of a flow of control when ultrasonic waves are transmitted and received in the embodiment.

First, in the control circuit 37, transmission channels are selected for use in transmitting ultrasound waves from the ultrasound probe 2 to the subject (step ST1). As described above, in the amplitude modulation, ultrasound waves are transmitted to the subject with the relative sound pressure ratio 1:2:1. Therefore, as long as this ratio can be maintained, transmission can be started from either even-numbered or odd-numbered channels. For convenience of explanation, first, transmission pulses are transmitted from the even-numbered channels to the subject.

The control circuit 37 feeds a control signal to the impedance control switching element 41 in all the channels (step ST2). As a result, the impedance control switching element 41 is turned on, and the line impedance of the receiving echo signal line 321 corresponding to each of all the channels in the receiving circuit 32 is kept lower than that in the case of receiving reflected waves.

Next, the control circuit 37 feeds a transmitted signal to even-numbered channels of the transmitting circuit 31. As a result, transmission pulses are transmitted from the even-numbered channels to the subject (step ST3).

Upon completion of the feeding of transmitted signals to the even-numbered channels (step ST4), the control circuit 37 terminates the feeding of control signals to the impedance control switching element 41 in all the channels (step ST5). Thereby, the impedance control switching element 41 is turned off. As the impedance control switching element 41 is turned off, the impedance, which has been kept low up to this point, becomes high. Thus, reflected waves can be received with high sensitivity.

Received signals (reflected waves) from the ultrasound probe are received in all channels while the line impedance in the receiving echo signal line 321 is high (step ST6). This is the end of the control of the impedance control circuit 4 when ultrasound waves are transmitted from the even-numbered channels.

Next, the control circuit 37 selects all the channels as transmission channels to be used for transmitting ultrasound waves from the ultrasound probe 2 to the subject (step ST7).

Then, the control circuit 37 feeds a control signal to the impedance control switching element 41 in all the channels (step ST8). As a result, the impedance control switching element 41 is turned on, and the line impedance of the receiving echo signal line 321 is kept lower than that in the case of receiving reflected waves.

The control circuit 37 feeds a transmitted signal to all the channels of the transmitting circuit 31. Thereby, transmission pulses are transmitted from all the channels to the subject (step ST9).

Upon completion of the feeding of transmitted signals to all the channels (step ST10), the control circuit 37 terminates the feeding of control signals to the impedance control switching element 41 in all the channels (step ST11). With this, the impedance control switching element 41 is turned off. As the impedance control switching element 41 is turned off, the impedance, which has been kept low up to this point, becomes high. Thus, reflected waves can be received with high sensitivity.

Received signals (reflected waves) from the ultrasound probe are received in all channels while the line impedance in the receiving echo signal line 321 is high (step ST12). This is the end of the control of the impedance control circuit 4 when ultrasound waves are transmitted from all the channels.

Next, the control circuit 37 selects odd-numbered channels as transmission channels to be used for transmitting ultrasound waves from the ultrasound probe 2 to the subject (step ST13 in FIG. 7).

Then, the control circuit 37 feeds a control signal to the impedance control switching element 41 in all the channels (step ST14). As a result, the impedance control switching element 41 is turned on, and the line impedance of the receiving echo signal line 321 is kept lower than that in the case of receiving reflected waves.

The control circuit 37 feeds a transmitted signal to the odd-numbered channels of the transmitting circuit 31. Thereby, transmission pulses are transmitted from the odd-numbered channels to the subject (step ST15).

Upon completion of the feeding of transmitted signals to the odd-numbered channels (step ST16), the control circuit 37 terminates the feeding of control signals to the impedance control switching element 41 in all the channels (step ST17). With this, the impedance control switching element 41 is turned off. As the impedance control switching element 41 is turned off, the impedance, which has been kept low up to this point, becomes high. Thus, reflected waves can be received with high sensitivity.

Received signals (reflected waves) from the ultrasound probe are received in all channels while the line impedance in the receiving echo signal line 321 is high (step ST18). This is the end of the control of the impedance control circuit 4 when ultrasound waves are transmitted from the odd-numbered channels.

Thus, the received signals necessary for generating one ultrasound image have been received. Then, it is checked whether ultrasound waves are continuously to be transmitted and received. When ultrasound waves are continuously to be transmitted and received (YES in step ST19), the process returns to step ST1 and the control circuit 37 repeats a series of control described above. On the other hand, when ultrasound waves are not to be transmitted and received (NO in step ST19), the generation of the ultrasound image is completed.

As described above, during the transmitting period in which ultrasound waves are transmitted from the transducers to the inside of the subject, the line impedance in the receiving echo signal line 321 of the receiving circuit 32 is set to be lower than that in the receiving period in which reflected waves generated inside the subject are received by the transducer. On the other hand, during the receiving period, regardless of transmission channels and non-transmission channels, the line impedance in the receiving echo signal, line 321 of the receiving circuit 32 of all the channels is set to be high. By this control, when amplitude modulation is performed for contrast harmonic imaging, it is possible to avoid crosstalk from a channel transmitting ultrasound waves to a channel not transmitting, thereby reducing transmission from the channel not transmitting. Thus, it is possible to generate an ultrasound image having a desired image quality as well as to prevent the deterioration of S/N ratio.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fait within the scope and spirit of the inventions.

What is claimed is:

1. An ultrasound diagnosis apparatus configured to transmit ultrasound waves to an inside of a subject from a plurality of transducers, each corresponding to one of a plurality of channels, and receive, by the transducers, reflected waves generated in the subject, the apparatus comprising:

a control circuit configured to control channels used to transmit the ultrasound waves and channels not used to transmit the ultrasound waves, among the plurality of channels; and
a receiving circuit configured to receive the reflected waves, wherein the receiving circuit includes
  a preamplifier configured to amplify the reflected waves, and
  an impedance control circuit located on an upstream side of the preamplifier and configured to set line impedance in a transmitting period, in which the ultrasound waves are transmitted from the transducers to the inside of the subject, to be lower than that in a receiving period, in which the reflected waves are received by the transducers.

2. The ultrasound diagnosis apparatus of claim 1, wherein the impedance control circuit includes an impedance control switching element that is connected to a receiving echo signal line and ground.

3. The ultrasound diagnosis apparatus of claim 2, wherein the impedance control circuit further includes a resistor between the receiving echo signal line and the impedance control switching element.

4. The ultrasound diagnosis apparatus of claim 1, wherein the receiving circuit further includes a line switching element configured to switch on and off to receive the reflected waves.

5. The ultrasound diagnosis apparatus of claim 2, wherein the control circuit is further configured to generate a control signal to turn on the impedance control switching element in the transmitting period, and output the control signal to the impedance control switching element such that the receiving circuit is grounded via the impedance control circuit to set the impedance from high to low.

6. The ultrasound diagnosis apparatus of claim 3, wherein the control circuit is further configured to generate a control signal to turn on the impedance control switching element in the transmitting period, and output the control signal to the impedance control switching element such that the receiving circuit is grounded via the impedance control circuit to set the impedance from high to low.

7. The ultrasound diagnosis apparatus of claim 1, wherein the impedance control circuit is configured to perform amplitude modulation in contrast harmonic imaging.

8. The ultrasound diagnosis apparatus of claim 2, wherein the impedance control circuit is configured to perform amplitude modulation in contrast harmonic imaging.

9. The ultrasound diagnosis apparatus of claim 3, wherein the impedance control circuit is configured to perform amplitude modulation in contrast harmonic imaging.

10. The ultrasound diagnosis apparatus of claim 5, wherein the control circuit is further configured to control the receiving circuit to be grounded via the impedance control circuit to set the impedance from high to low when performing amplitude modulation in contrast harmonic imaging.

11. The ultrasound diagnosis apparatus of claim 6, wherein the control circuit is further configured to control the receiving circuit to be grounded via the impedance control circuit to set the impedance from high to low when performing amplitude modulation in contrast harmonic imaging.

12. The ultrasound diagnosis apparatus of claim 1, wherein the impedance control circuit is configured to set the line impedance under control of the control circuit.

* * * * *